(12) United States Patent
Limbach et al.

(10) Patent No.: US 8,642,803 B2
(45) Date of Patent: Feb. 4, 2014

(54) PREPARATION OF ETHYLENICALLY UNSATURATED CARBOXYLIC SALTS BY CARBOXYLATION OF ALKENES

(75) Inventors: Michael Limbach, Worms (DE); Jeremie Miller, Mannheim (DE); Stephan Schunk, Heidelberg-Rohrbach (DE)

(73) Assignee: BASF SE, Ludwigshafen (DE)

( * ) Notice: Subject to any disclaimer, the term of this patent is extended or adjusted under 35 U.S.C. 154(b) by 460 days.

(21) Appl. No.: 13/040,043

(22) Filed: Mar. 3, 2011

(65) Prior Publication Data

US 2011/0218359 A1 Sep. 8, 2011

Related U.S. Application Data

(60) Provisional application No. 61/309,917, filed on Mar. 3, 2010.

(51) Int. Cl.
*C07C 51/15* (2006.01)
*C07C 57/02* (2006.01)
*C07C 57/03* (2006.01)
*C07C 57/04* (2006.01)

(52) U.S. Cl.
USPC .......................... 562/522; 562/521; 562/598

(58) Field of Classification Search
None
See application file for complete search history.

(56) References Cited

U.S. PATENT DOCUMENTS

| 2007/0219391 A1 | 9/2007 | Lilga et al. |
| 2007/0287747 A1 | 12/2007 | Finmans et al. |
| 2011/0218323 A1 | 9/2011 | Dahmen et al. |

FOREIGN PATENT DOCUMENTS

| DE | 3432082 | 3/1988 |
| DE | 10221203 | 7/2003 |
| DE | 103 30 217 | 12/2004 |
| WO | WO 2010/054988 A2 | 5/2010 |
| WO | WO 2010/136551 A2 | 12/2010 |
| WO | WO 2011/051374 A1 | 5/2011 |

OTHER PUBLICATIONS

Takakazu Yamamoto, et al., "Preparation and Properties of Phosphine Complexes of Nickel-Containing Cyclic Amides and Esters", J. Am. Chem. Soc., vol. 102, 1980, pp. 7448-7456.
David C. Graham, et al., "Production of Acrylic Acid through Nickle-Mediated Coupling of Ethylene and Carbon Dioxide—A DFT Study", Organometallics, vol. 26, 2007, pp. 6784-6792.
Heinz Hoberg, et al., "Nickle(0)-Induzierte C-C-Verknüpfung Zwischen Kohlendioxid Und Ethylen Sowie Mono-Oder Di-Substituierten Alkenen", Journal of Organometallic Chemistry, vol. 251, 1983, pp. C51-053 (with English summary).
Heinz Hoberg, et al., "Nickle(0)-Induzierte C-C-Verknüpfung Zwischen Alkenen Und Kohlendioxid", Journal of Organometallic Chemistry, vol. 236, 1982, pp. C28-C30, (with English summary).
U.S. Appl. No. 13/192,797, filed Jul. 28, 2011, Pantouflas, et al.
U.S. Appl. No. 13/479,961, filed May 24, 2012, Stroefer, et al.
U.S. Appl. No. 13/375,019, filed Nov. 29, 2011, Karpov, et al.
U.S. Appl. No. 13/503,548, filed Apr. 23, 2012, Mueller, et al.
International Search Report issued Oct. 14, 2011 in PCT/EP2011/053229.
Cokoja et al., Angew Chem Int ED 2011, 50(37), 8510-8537.

*Primary Examiner* — Yevegeny Valenrod
(74) *Attorney, Agent, or Firm* — Oblon, Spivak, McClelland, Maier & Neustadt, L.L.P.

(57) ABSTRACT

A process for preparing an alkali metal or alkaline earth metal salt of an α,β-ethylenically unsaturated carboxylic acid, wherein a) an alkene, carbon dioxide and a carboxylation catalyst are converted to an alkene/carbon dioxide/carboxylation catalyst adduct, b) the adduct is decomposed to release the carboxylation catalyst with an auxiliary base to give the auxiliary base salt of the α,β-ethylenically unsaturated carboxylic acid, c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid. Salts of α,β-ethylenically unsaturated carboxylic acids, such as sodium acrylate in particular, are required in large amounts, for example, for production of water-absorbing resins.

15 Claims, No Drawings

PREPARATION OF ETHYLENICALLY UNSATURATED CARBOXYLIC SALTS BY CARBOXYLATION OF ALKENES

The invention relates to a process for preparing an alkali metal or alkaline earth metal salt of an α,β-ethylenically unsaturated carboxylic acid by direct carboxylation of alkenes, especially to a process for preparing an alkali metal or alkaline earth metal salt of acrylic acid by direct carboxylation of ethene.

The direct addition of $CO_2$ onto ethylene (scheme 1) is industrially unattractive owing to thermodynamic limitations (ΔG=34.5 kJ/mol) and the unfavorable equilibrium, which is almost completely to the side of the reactants at room temperature ($K_{293}=7\times10^{-7}$).

Scheme 1:

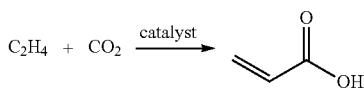

Yamamoto et al. (*J. Am. Chem. Soc.* 1980, 102, 7448) showed that the reaction of acrylic acid with a homogeneous Ni(0) species such as bis(1,5-cyclooctadiene)nickel in the presence of a tertiary phosphine ligand at temperatures above 0° C. forms the stable five-membered nickelalactone ring A, known as the "Hoberg complex" (scheme 2). At temperatures below 0° C., the same reaction affords an equimolar mixture of the lactone A and of the acyclic π complex B. The thermal splitting of A to give free acrylic acid did not succeed. Theoretical chemistry studies by Buntine et al. (*Organometallics* 2007, 26, 6784) show the ~40 kcal/mol$^{-1}$ increase in stability of the intermediate nickelalactone A compared to the acrylic acid reaction product.

The same nickelalactone A arises from the direct coupling of $CO_2$ and ethylene, as found by Hoberg (*J. Organomet. Chem.* 1983, C51). The same reaction is observed with the basic 2,2'-bipyridine ligand and an Ni(0) species on other alkenes or alkynes (e.g. norbornene) and the nickelacycles derived therefrom. These are isolable as stable solids (*J. Organomet. Chem.* 1982, C28), which demonstrates the exceptional stability of these compounds.

Scheme 2:

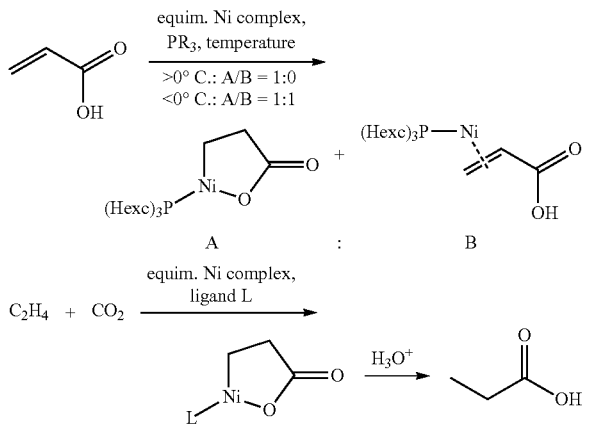

The treatment of such stable nickelalactones with aqueous mineral acids gives propionic acid in the case of cycle A, but not acrylic acid. This suggests that the β-hydride elimination needed to form acrylic acid and derivatives thereof from the complex A is hindered. Accordingly, no catalytic variant of this reaction has been described as yet.

It was an object of the invention to specify a process suitable for industrial preparation of α,β-ethylenically unsaturated carboxylic acid derivatives, which uses the reaction of $CO_2$ and an alkene.

It has now been found that additional use of an auxiliary in the form of a base can shift the equilibrium of the reaction of $CO_2$ and alkene to the product side. The formation of a salt of the α,β-ethylenically unsaturated carboxylic acid appears to thermodynamically favor the reaction. Salts of α,β-ethylenically unsaturated carboxylic acids, such as sodium acrylate in particular, are required in large amounts, for example, for production of water-absorbing resins (known as superabsorbents).

The invention provides a process for preparing an alkali metal or alkaline earth metal salt of an α,β-ethylenically unsaturated carboxylic acid, wherein a) an alkene, carbon dioxide and a carboxylation catalyst are converted to an alkene/carbon dioxide/carboxylation catalyst adduct, b) the adduct is decomposed to release the carboxylation catalyst with an auxiliary base to give the auxiliary base salt of the α,β-ethylenically unsaturated carboxylic acid, c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid.

Steps a) and b) of the process according to the invention can be performed successively, but preferably proceed simultaneously as a result of contacting of alkene, carbon dioxide and carboxylation catalyst in the presence of the auxiliary base in a carboxylation reactor.

The expression "alkene/carbon dioxide/carboxylation catalyst adduct" should be interpreted in a broad sense and may comprise compounds with structures similar to the "Hoberg complex" mentioned at the outset or compounds of unknown structure. The expression shall comprise isolable compounds and unstable intermediates.

Suitable alkenes comprise at least 2 carbon atoms, for example 2 to 8 carbon atoms or 2 to 6 carbon atoms, and at least one ethylenically unsaturated double bond. The double bond is preferably in the terminal position. The alkene may also be a diene, in which case at least one carbon-carbon double bond is terminal and the other double bond is anywhere along the carbon skeleton. Suitable alkenes are, for example, ethene, propene, isobutene and piperylene. The alkene for use in the carboxylation is generally gaseous or liquid under the carboxylation conditions.

In a preferred embodiment, the alkene is ethene. The process according to the invention makes it possible to obtain concentrated aqueous solutions of alkali metal or alkaline earth metal acrylates, especially sodium acrylate, in high purity and yield. In another embodiment, it is possible by the process according to the invention to obtain, for example, the potassium salt of sorbic acid from piperylene and KOH.

The carbon dioxide for use in the reaction can be used in gaseous, liquid or supercritical form. It is also possible to use carbon dioxide-comprising gas mixtures available on the industrial scale, provided that they are substantially free of carbon monoxide.

Carbon dioxide and alkene may also comprise inert gases, such as nitrogen or noble gases. Advantageously, however, the content thereof is less than 10 mol % based on the total amount of carbon dioxide and alkene in the reactor.

The molar ratio of carbon dioxide to alkene in the feed of the reactor is generally 0.1 to 10 and preferably 0.5 to 3.

The auxiliary base may be an organic or inorganic auxiliary base. Suitable auxiliary bases are anionic bases (generally in the form of salts thereof with inorganic or organic ammonium ions or alkali metals or alkaline earth metals) or neutral bases. Inorganic anionic bases include carbonates, phosphates, nitrates or halides; examples of organic anionic bases include phenoxides, carboxylates, sulfates of organic molecular units, sulfonates, phosphates, phosphonates.

Organic neutral bases include primary, secondary or tertiary amines, and also ethers, esters, imines, amides, carbonyl compounds, carboxylates or carbon monoxide.

The auxiliary base is preferably a primary, secondary or tertiary amine. The auxiliary base is most preferably a tertiary amine. Suitable tertiary amines have the general formula (I)

$$NR^1R^2R^3 \quad (I),$$

in which the $R^1$ to $R^3$ radicals are the same or different and are each independently an unbranched or branched, acyclic or cyclic, aliphatic, araliphatic or aromatic radical having in each case 1 to 16 carbon atoms, preferably 1 to 12 carbon atoms, where individual carbon atoms may each independently also be replaced by a heteroatom selected from the group of —O— and >N—, and two or all three radicals may also be joined to one another to form a chain comprising at least four atoms in each case.

Examples of suitable amines include:

Tri-n-propylamine, tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine.

Dimethyldecylamine, dimethyldodecylamine, dimethyltetradecylamine, ethyldi(2-propyl)amine, dioctylmethylamine, dihexylmethylamine.

Tricyclopentylamine, tricyclohexylamine, tricycloheptylamine, tricyclooctylamine, and the derivatives thereof substituted by one or more methyl, ethyl, 1-propyl, 2-propyl, 1-butyl, 2-butyl or 2-methyl-2-propyl groups.

Dimethylcyclohexylamine, methyldicyclohexylamine, diethylcyclohexylamine, ethyldicyclohexylamine, dimethylcyclopentylamine, methyldicyclopentylamine.

Triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis-(2-ethylhexyl)phenylamine, tribenzylamine, methyldibenzylamine, ethyldibenzylamine and the derivatives thereof substituted by one or more methyl, ethyl, 1-propyl, 2-propyl, 1-butyl, 2-butyl or 2-methyl-2-propyl groups.

N—$C_1$- to —$C_{12}$-alkylpiperidines, N,N'-di-$C_1$- to —$C_{12}$-alkylpiperazines, N—$C_1$- to —$C_{12}$-alkylpyrrolidines, N—$C_1$- to —$C_{12}$-alkylimidazoles, and the derivatives thereof substituted by one or more methyl, ethyl, 1-propyl, 2-propyl, 1-butyl, 2-butyl or 2-methyl-2-propyl groups.

1,8-Diazabicyclo[5.4.0]undec-7-ene (DBU), 1,4-diazabicyclo[2.2.2]octane (DABCO) N-methyl-8-azabicyclo[3.2.1]octane (tropane), N-methyl-9-azabicyclo[3.3.1]nonane (granatane), 1-azabicyclo[2.2.2]octane (quinuclidine).

In the process according to the invention, it is of course also possible to use mixtures of different bases, especially of different tertiary amines (I).

Preferably, at least one of the $R^1$ to $R^3$ radicals bears two hydrogen atoms on the α-carbon atom.

The tertiary amine used in the process according to the invention is most preferably an amine of the general formula (I) in which the $R^1$ to $R^3$ radicals are each independently selected from the group of $C_1$- to $C_{12}$-alkyl, $C_5$- to $C_8$-cycloalkyl, benzyl and phenyl.

The amount of the auxiliary base for use in the process according to the invention, preferably of a tertiary amine, is generally 5 to 95% by weight, preferably 20 to 60% by weight, based in each case on the overall liquid reaction mixture in the reactor.

In general, the carboxylation catalyst comprises, as the active metal, at least one element from groups 4 (preferably Ti, Zr), 6 (preferably Cr, Mo, W), 7 (preferably Re), 8 (preferably Fe, Ru), 9 (preferably Co, Rh) and 10 (preferably Ni, Pd) of the Periodic Table of the Elements. Preference is given to nickel, cobalt, iron, rhodium, ruthenium, palladium, rhenium, tungsten. Particular preference is given to nickel, cobalt, iron, rhodium, ruthenium.

The role of these active metals is the activation of $CO_2$ and alkene in order to form a C—C bond between $CO_2$ and the alkene. This activation can be effected at one or more active sites. After formation of this "Hoberg"-like complex, it can be eliminated in the presence of the auxiliary base used in accordance with the invention as the auxiliary base salt of the α,β-ethylenically unsaturated carboxylic acid.

In one embodiment, the carboxylation catalyst used is a heterogeneous catalyst. Heterogeneous carboxylation catalysts may be present in the form of supported catalysts or in the form of unsupported catalysts. A supported catalyst consists of a catalyst support and one or more active metals, and optionally one or more additives.

The proportion by weight of active metal, based on the sum of active metal, support material and additives, is preferably 0.01 to 40% by weight, more preferably 0.1 to 30% by weight, most preferably 0.5 to 10% by weight.

The proportion by weight of additives, based on the sum of active metal, support material and additives, is preferably 0.001 to 20% by weight, more preferably 0.01 to 10% by weight, most preferably 0.1 to 5% by weight.

Typical processes for preparing supported catalysts are impregnation processes, for example incipient wetness, adsorption processes, for example equilibrium adsorption, precipitation processes, mechanical processes, for example the grinding of active metal precursor and support material, and further processes known to those skilled in the art.

Suitable inorganic additives may include: magnesium, calcium, strontium, barium, lanthanum, lanthanoids, manganese, copper, silver, zinc, boron, aluminum, silicon, tin, lead, phosphorus, antimony, bismuth, sulfur and selenium. Suitable organic additives may include: carboxylic acids, salts of carboxylic acids, polymers, for example PVP (polyvinylpyrrolidone), PEG (polyethylene glycol) or PVA (polyvinyl alcohol), amines, diamines, triamines, imines.

Suitable support materials may include: refractory oxides, for example zinc oxide, zirconium oxide, cerium oxide, cerium zirconium oxides, silica, alumina, silica-alumina, zeolites, sheet silicates, hydrotalcites, magnesium oxide, titanium dioxide, tungsten oxide, calcium oxide, iron oxides, for example magnetite, nickel oxides, cobalt oxides, phosphates of the main group and transition group elements, carbides, nitrides, organic polymers such as Nafion or functionalized polystyrene, metallic support materials such as metal sheets or meshes, MOFs (metal-organic frameworks) or composite materials of the aforementioned materials.

Preference is given to refractory oxides, for example zinc oxide, zirconium oxide, cerium oxide, cerium zirconium oxides, silica, alumina, silica-alumina, zeolites, sheet silicates, hydrotalcites, magnesium oxide, titanium dioxide, tungsten oxide, calcium oxide, iron oxides, for example magnetite, nickel oxides or cobalt oxides.

The support materials can be used, for example, in the form of powder, granules or tablets, or in another form known to those skilled in the art.

According to the invention, it is also possible to use unsupported catalysts. Such materials can be prepared, for example, by precipitation processes or other processes known to those skilled in the art. Such catalysts are preferably present in metallic and/or oxidic form.

When a heterogeneous catalyst is used in the process according to the invention, it preferably remains in the carboxylation reactor. This is enabled, for example, by virtue of it being present in the form of a fixed bed catalyst fixed within the reactor, or, in the case of a suspension catalyst, by virtue of it being retained within the reactor by a suitable sieve or a suitable filter.

In preferred embodiments, the carboxylation catalyst used is a homogeneous catalyst. Homogeneous catalysts are generally complexes of the metals. In the case of a homogeneous catalyst, the active metals are present homogeneously dissolved in the reaction mixture in the form of complex-type compounds.

The homogeneous carboxylation catalyst suitably comprises at least one phosphine ligand. The phosphine ligands may be mono-, bi- or polydendate, i.e. the ligands have one, two or more than two, e.g. three, tertiary trivalent phosphorus atoms. The phosphorus atoms may be unbranched or branched, acyclic or cyclic, aliphatic radicals having 1 to 18 carbon atoms.

Suitable monodentate phosphine ligands have, for example, the formula (II)

$PR^4R^5R^6$ (II)

in which $R^4$, $R^5$ and $R^6$ are each independently $C_1$-$C_{12}$-alkyl, $C_3$-$C_{12}$-cycloalkyl, aryl, aryl-$C_1$-$C_4$-alkyl, where cycloalkyl, aryl and the aryl moiety of aryl-$C_1$-$C_4$-alkyl are unsubstituted or may bear 1, 2, 3 or 4 identical or different substituents, for example Cl, Br, I, F, $C_1$-$C_8$-alkyl or $C_1$-$C_4$-alkoxy.

Suitable $R^4$, $R^5$ and $R^6$ radicals are, for example, $C_1$-$C_{12}$-alkyl such as methyl, ethyl, 1-propyl, 2-propyl, 1-butyl, 2-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, $C_3$-$C_{10}$-cycloalkyl which is unsubstituted or may bear a $C_1$-$C_4$-alkyl group, for example cyclopentyl, methylcyclopentyl, cyclohexyl, methylcyclohexyl, cycloheptyl, cyclooctyl and norbornyl, aryl which is unsubstituted or may bear one or two substituents selected from chlorine, $C_1$-$C_8$-alkyl and $C_1$-$C_8$-alkoxy, such as phenyl, napthyl, tolyl, xylyl, chlorophenyl or anisyl.

Examples of suitable phosphine ligands of the formula (II) comprise trialkylphosphines such as tri-n-propylphosphine, tri-n-butylphosphine, tri-tert-butylphosphine or trioctylphosphine, tricycloalkylphosphines such as tricyclohexylphosphine or tricyclododecylphosphine, triaryiphosphines such as triphenylphosphine, tritolylphosphine, trianisylphosphine, trinaphthylphosphine or di(chlorophenyl)phenylphosphine, and dialkylarylphosphines such as diethylphenylphosphine or dibutylphenylphosphine. $R^4$, $R^5$ and $R^6$ preferably have the same definition.

Suitable bidentate phosphine ligands have, for example, the formula (III)

$R^7R^8P$-A-$PR^9R^{10}$ (III)

in which A is $C_1$-$C_4$-alkylene and $R^7$, $R^8$, $R^9$ and $R^{10}$ are each independently as defined for $R^4$, $R^5$ and $R^6$.

Examples of bidentate phosphines are 1,2-bis(dicyclohexylphosphino)ethane, 1,2-bis(dicyclohexylphosphino)methane, 1,2-bis(dimethylphosphino)ethane, 1,2-bis(dimethylphosphino)methane, 1,2-bis(di-tert-butylphosphino)methane or 1,2-bis(diisopropylphosphino)propane.

The organometallic complex may comprise one or more, for example two, three or four, of the abovementioned phosphine groups with at least one unbranched or branched, acylic or cyclic, aliphatic radical.

In addition, at least one equivalent of the auxiliary base itself may function as a ligand on the metal of the homogeneous complex.

Alternatively, the carboxylation catalyst comprises at least one N-heterocyclic carbene ligand. Here, N-heterocyclic carbenes of the general formula (IV) or (V) function as ligands on the metal:

(IV)

(V)

in which $R^{11}$ and $R^{12}$ are each alkyl or aryl, $R^{13}$, $R^{14}$, $R^{15}$ and $R^{16}$ are each independently hydrogen, alkyl or aryl, or two of the $R^{13}$ to $R^{16}$ radicals form a saturated five- to seven-membered ring, where the two other radicals are each independently hydrogen or methyl, $R^{17}$ and $R^{18}$ are each independently hydrogen, alkyl or aryl, or $R^{17}$ and $R^{18}$, together with the carbon atoms to which they are bonded, are a fused ring system with 1 or 2 aromatic rings.

In addition to the ligands described above, the catalyst may also have at least one further ligand which is selected from halides, amines, carboxylates, acetylacetonate, aryl- or alkylsulfonates, hydride, CO, olefins, dienes, cycloolefins, nitriles, aromatics and heteroaromatics, ethers, $PF_3$, phospholes, phosphabenzenes and mono-, di- and polydentate phosphinite, phosphonite, phosphoramidite and phosphite ligands.

The homogeneous catalysts can be obtained either directly in their active form or preceding from customary standard complexes, for example $[M(p\text{-cymene})Cl_2]_2$, $[M(\text{benzene})Cl_2]_n$, $[M(COD)(allyl)]$, $[MCl_3 \times H_2O]$, $[M(\text{acetylacetonate})_3]$, $[M(DMSO)_4Cl_2]$ where M is an element of group 4, 6, 7, 8, 9 or 10 of the Periodic Table with addition of the corresponding ligand(s) only under reaction conditions.

In the case of use of homogeneous catalysts, the amount used of the metal complexes mentioned in the organometallic complex is generally 0.1 to 5000 ppm by weight, preferably 1 to 800 ppm by weight and more preferably 5 to 500 ppm by weight, based in each case on the overall liquid reaction mixture in the reactor.

The carboxylation reactors used may in principle be all reactors which are suitable for gas/liquid reactions or liquid/ liquid reactions at the given temperature and under the given pressure. Suitable standard reactors for liquid-liquid reaction systems are specified, for example, in K. D. Henkel, "Reactor Types and Their Industrial Application", in Ullmann's Encyclopedia of Industrial Chemistry 2005, Wiley VCH Verlag GmbH & Co KGaA, DOI: 10.1002/14356007.b04_087, chapter 3.3 "Reactors for gas-liquid reactions". Examples include stirred tank reactors, tubular reactors or bubble column reactors.

The carboxylation can be performed batchwise or continuously. In batchwise mode, the reactor is filled with the desired liquid or optionally solid feedstocks and auxiliaries, and then carbon dioxide and alkene are injected to the desired pressure and the desired temperature. After the end of the reaction, the reactor is generally decompressed.

In continuous mode, the feedstocks and auxiliaries, including the carbon dioxide and alkene, are added continuously. Any heterogeneous carboxylation catalyst to be used is preferably present fixed within the reactor. Accordingly, the liquid phase is removed continuously from the reactor, such that the liquid level in the reactor remains the same on average.

Steps a) and b) are preferably performed in the liquid or supercritical phase at pressures between 1 and 150 bar, preferably at pressures between 1 and 100 bar, more preferably at pressures between 1 and 60 bar. Steps a) and b) of the process according to the invention are preferably performed at temperatures between −20° C. and 300° C., preferably at temperatures between 20° C. and 250° C., more preferably at temperatures between 40° C. and 200° C.

In order to achieve good mixing of the reactants and of the medium which comprises the carboxylation catalyst and the auxiliary base, suitable apparatus can be used. Such apparatus may be mechanical stirred apparatus with one or more stirrers with or without baffles, packed or non-packed bubble columns, packed or non-packed flow tubes with or without static mixers, or other useful apparatus known to those skilled in the art for these process steps. The use of baffles and delay structures is explicitly incorporated into the process according to the invention.

The $CO_2$ and alkene reactants can be fed to the reaction medium either together or spatially separately. Such a spatial separation can be accomplished, for example in a stirred tank, in a simple manner by means of two or more separate inlets. When more than one tank is used, for example, there may be different media charges in different tanks. Separation of the addition of the $CO_2$ and alkene reactants in terms of time is also possible in the process according to the invention. Such a time separation can be accomplished, for example, in a stirred tank by staggering the charging with the reactants. In the case of use of flow tubes or apparatus of a similar kind, such charging can be effected, for example, at different sites in the flow tube; such a variation of the addition sites is an elegant way of adding the reactants as a function of residence time.

In steps a) and b), one or more immiscible or only partly miscible liquid phases can be used. The use of supercritical media and ionic liquids and the establishment of conditions which promote formation of such states are explicitly incorporated into the process. The application of phase transfer catalysis and/or the use of surfactants are explicitly incorporated into the process according to the invention.

In a preferred embodiment, the auxiliary base salt, formed in step b), of the α,β-ethylenically unsaturated carboxylic acid is removed from the reaction medium. The removal of the auxiliary base salt preferably comprises a liquid-liquid phase separation into a first liquid phase in which the auxiliary base salt of the α,β-ethylenically unsaturated carboxylic acid is enriched, and a second liquid phase in which the auxiliary base is enriched.

In the case of use of a homogeneous carboxylation catalyst, it is preferably selected such that it is enriched together with the auxiliary base in the second liquid phase. "Enriched" is understood to mean a partition coefficient P of the homogeneous catalyst of >1. The partition coefficient is preferably ≥10 and more preferably ≥20.

$$P = \frac{[\text{Concentration of homogeneous catalyst in the second liquid phase}]}{[\text{Concentration of homogeneous catalyst in the first liquid phase}]}$$

The homogeneous catalyst is generally selected by a simple experiment in which the partition coefficient of the desired homogeneous catalyst is determined experimentally under the planned process conditions.

The liquid-liquid phase separation is promoted by the additional use of a polar solvent in which the auxiliary base salt of the α,β-ethylenically unsaturated carboxylic acid has good solubility and which has zero or only limited miscibility with the second liquid phase in which the auxiliary base is enriched. The polar solvent should be selected, or matched with the auxiliary base, such that the polar solvent is present in enriched form in the first liquid phase. "Enriched" is understood to mean a proportion by weight of >50% of the polar solvent in the first liquid phase based on the total amount of polar solvent in both liquid phases. The proportion by weight is preferably >90%, more preferably >95% and most preferably >97%. The polar solvent is generally selected by simple tests in which the partition of the polar solvent in the two liquid phases is determined experimentally under the process conditions.

Preferred substance classes which are suitable as polar solvents are diols and the carboxylic esters thereof, polyols and the carboxylic esters thereof, sulfones, sulfoxides, open-chain or cyclic amides, and mixtures of the substance classes mentioned.

Examples of suitable diols and polyols are ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

Examples of suitable sulfoxides are dialkyl sulfoxides, preferably $C_1$- to $C_6$-dialkyl sulfoxides, especially dimethyl sulfoxide.

Examples of suitable open-chain or cyclic amides are formamide, N-methylformamide, N,N-dimethylformamide, N-methylpyrrolidone, acetamide and N-methylcaprolactam.

If desired, it is possible also to use a solvent which is immiscible or has only limited miscibility with the polar solvent. Suitable solvents are in principle those which (i) are chemically inert with regard to the carboxylation of the alkene, (ii) in which the auxiliary base and, in the case of use of a homogeneous catalyst, this too have good solubility, (iii) in which the auxiliary base salt of the α,β-ethylenically unsaturated carboxylic acid has good solubility and (iv) which are immiscible or only have limited miscibility with the polar solvent. Useful solvents are therefore in principle chemically inert, nonpolar solvents, for instance aliphatic, aromatic or araliphatic hydrocarbons, for example octane and higher alkanes, toluene, xylene. If the auxiliary base itself is present in liquid form in all process stages in the process according to the invention, the use of a solvent which is immiscible or has only limited miscibility with the polar solvent is unnecessary.

In the case of use of a homogeneous carboxylation catalyst, suitable selection of the auxiliary base and optionally of a polar solvent and/or of a solvent which is immiscible or has only limited miscibility therewith, for example, achieves the effect that the carboxylation catalyst is enriched in the second liquid phase. For instance, it can be separated by phase separation from the auxiliary base salt of the α,β-unsaturated acid and be recycled to the reactor with no further workup steps. Owing to the rapid removal of the catalyst from the auxiliary base salt formed from the α,β-unsaturated acid, a reverse reaction with decomposition to carbon dioxide and alkene is suppressed. In addition, the retention or removal of the catalyst, owing to the formation of two liquid phases, minimizes losses of catalyst and hence losses of active metal.

To remove the first liquid phase, the procedure may be to only conduct the first liquid phase out of the carboxylation reactor and to leave the second liquid phase within the carboxylation reactor. Alternatively, a liquid-liquid mixed-phase stream can be conducted out of the carboxylation reactor and the liquid-liquid phase separation can be performed in a suitable apparatus outside the carboxylation reactor. The two liquid phases are generally separated by gravimetric phase separation. Suitable examples for this purpose are standard apparatus and standard methods which can be found, for example, in E. Müller et al., "Liquid-Liquid Extraction", in Ullmann's Encyclopedia of Industrial Chemistry, 2005, Wiley-VCH Verlag GmbH & Co. KGaA, DOI:10.1002/14356007.b03_06, chapter 3 "Apparatus". In general, the first liquid phase enriched with the auxiliary base salt of the α,β-ethylenically unsaturated carboxylic acid is heavier and forms the lower phase. The second liquid phase can subsequently be recycled into the carboxylation reactor.

In step c), the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid. Suitable alkali metal or alkaline earth metal bases are especially alkali metal or alkaline earth metal hydroxides, carbonates, hydrogencarbonates or oxides. Suitable alkali metal and alkaline earth metal hydroxides are, for example, sodium hydroxide, potassium hydroxide, magnesium hydroxide and calcium hydroxide. Suitable alkali metal and alkaline earth metal carbonates are, for example, lithium carbonate, sodium carbonate, potassium carbonate and calcium carbonate. Suitable alkali metal hydrogencarbonates are, for example, sodium hydrogencarbonate or potassium hydrogencarbonate. Suitable alkali metal and alkaline earth metal oxides are, for example, lithium oxide, sodium oxide, calcium oxide and magnesium oxide. Particular preference is given to sodium hydroxide.

The alkali metal or alkaline earth metal base is added under conditions which are suitable for enabling base exchange between the auxiliary base salt of the α,β-ethylenically unsaturated carboxylic acid and the alkali metal or alkaline earth metal base. Step c) of the process according to the invention is preferably performed in the liquid or supercritical phase at pressures between 1 and 150 bar, preferably at pressures between 1 and 100 bar, more preferably at pressures between 1 and 60 bar. Step c) of the process according to the invention is preferably performed at temperatures between −20° C. and 300° C., preferably at temperatures between 20° C. and 250° C., more preferably at temperatures between 40° C. and 200° C. The reaction conditions of step c) may be the same as or different than those of steps a) and b).

In step c), one or more immiscible or only partly miscible liquid phases can be used. Typically, such immiscible or only partly miscible liquid phases are an organic phase and an aqueous phase. The use of supercritical media and ionic liquids, and the establishment of conditions which promote the formation of such states, is explicitly incorporated into the process.

The alkali metal or alkaline earth metal salt of the α,β-ethylenically unsaturated carboxylic acid is preferably separated from the auxiliary base released via the separation thereof into two different phases. It is thus possible, for example, to remove the alkali metal or alkaline earth metal salt of the α,β-ethylenically unsaturated carboxylic acid in a polar aqueous phase, and the auxiliary base in an organic phase. The use of effects which facilitate separation, such as the change of phase of ionic liquids or of supercritical media, is explicitly incorporated into the process. Pressure or temperature changes which have a favorable effect on the separation of the phases are explicitly incorporated into the process.

The auxiliary base released is recycled into step b). This recycling is undertaken under conditions which are favorable for the process.

The first liquid phase removed is preferably treated with an aqueous solution of the alkali metal or alkaline earth metal base to obtain an aqueous solution of the alkali metal or alkaline earth metal salt of the α,β-ethylenically unsaturated carboxylic acid and an organic phase which comprises the auxiliary base.

The first liquid phase is generally immiscible or has only limited miscibility with the solution of the alkali metal or alkaline earth metal base, such that the treatment can appropriately be performed in the form of a liquid-liquid extraction. Liquid-liquid extraction can be effected in all apparatus suitable for this purpose, such as stirred vessels, extractors or percolators. An aqueous phase is obtained, which comprises an aqueous solution of the alkali metal or alkaline earth metal salt of the α,β-ethylenically unsaturated carboxylic acid, and an organic phase which comprises the auxiliary base.

The auxiliary base released is recycled back into the carboxylation reactor. As a result of the simpler process design, the production plant required to perform the process according to the invention requires less space and the use of fewer apparatuses compared to the prior art. It has a lower capital cost and a lower energy demand.

In another embodiment, in step c), the reaction medium (without preceding removal of the auxiliary base salt of the α,β-ethylenically unsaturated carboxylic acid) can be extracted with an aqueous solution of the alkali metal or alkaline earth metal base to obtain an aqueous solution of the alkali metal or alkaline earth metal salt of the α,β-ethylenically unsaturated carboxylic acid. The extraction can be effected directly within the carboxylation reactor, simultaneously with steps a) and b). For this purpose, a solution of the alkali metal or alkaline earth metal base can be introduced into the carboxylation reactor, the reaction medium can be extracted in the carboxylation reactor with the solution of the alkali metal or alkaline earth metal base, and an aqueous solution of the alkali metal or alkaline earth metal salt of the α,β-ethylenically unsaturated carboxylic acid can be removed from the carboxylation reactor.

The invention claimed is:

1. A process for preparing an alkali metal or alkaline earth metal salt of an α,β-ethylenically unsaturated carboxylic acid, wherein a) an alkene, carbon dioxide and a carboxylation catalyst are converted to an alkene/carbon dioxide/carboxylation catalyst adduct,
b) the adduct is decomposed to release the carboxylation catalyst with an auxiliary base to give the auxiliary base salt of the α,β-ethylenically unsaturated carboxylic acid,
c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid.

2. The process according to claim 1, wherein the auxiliary base salt, formed in step b), of the α,β-ethylenically unsaturated carboxylic acid is removed from the reaction medium.

3. The process according to claim 2, wherein the removal comprises a liquid-liquid phase separation into a first liquid phase in which the auxiliary base salt of the α,β-ethylenically unsaturated carboxylic acid is enriched, and a second liquid phase in which the auxiliary base is enriched.

4. The process according to claim 3, wherein the first liquid phase removed is treated in step c) with an aqueous solution of the alkali metal or alkaline earth metal base to obtain an aqueous solution of the alkali metal or alkaline earth metal salt of the α,β-ethylenically unsaturated carboxylic acid and an organic phase which comprises the auxiliary base.

5. The process according to claim 1, wherein the reaction medium is extracted in step c) with an aqueous solution of alkali metal or alkaline earth metal base to obtain an aqueous solution of the alkali metal or alkaline earth metal salt of the α,β-ethylenically unsaturated carboxylic acid.

6. The process according to claim 1, wherein the auxiliary base is a tertiary amine.

7. The process according to claim 6, wherein the tertiary amine has the general formula (I)

$$NR^1R^2R^3 \qquad (I)$$

in which the $R^1$ to $R^3$ radicals are the same or different and are each independently an unbranched or branched, acyclic or cyclic, aliphatic, araliphatic or aromatic radical having in each case 1 to 16 carbon atoms, where individual carbon atoms may each independently also be replaced by a hetero group selected from the group of —O— and >N—, and two or all three radicals may also be joined to one another to form a chain comprising at least four atoms in each case, uses.

8. The process according to claim 1, wherein the carboxylation catalyst comprises at least one element from groups 4, 6, 7, 8, 9 and 10 of the Periodic Table of the Elements.

9. The process according to claim 8, wherein the carboxylation catalyst comprises a complex of $Ni^0$.

10. The process according to claim 1, wherein the carboxylation catalyst used is a heterogeneous catalyst.

11. The process according to claim 1, wherein the carboxylation catalyst used is a homogeneous catalyst.

12. The process according to claim 3, wherein the carboxylation catalyst used is a homogeneous catalyst and the carboxylation catalyst is enriched in the second liquid phase.

13. The process according to claim 1, wherein the carboxylation catalyst comprises at least one phosphine ligand.

14. The process according to claim 1, wherein the carboxylation catalyst comprises at least one N-heterocyclic carbene ligand.

15. The process according to claim 1, wherein the alkene is ethene and the α,β-ethylenically unsaturated carboxylic acid is acrylic acid.

* * * * *